United States Patent
Zinn

(10) Patent No.: US 8,622,980 B2
(45) Date of Patent: Jan. 7, 2014

(54) IMPLANTABLE PORT WITH A PIVOTABLY COUPLED STEM

(75) Inventor: Kenneth M. Zinn, Westport, CT (US)

(73) Assignee: Medical Components, Inc., Harleysville, PA (US)

( * ) Notice: Subject to any disclaimer, the term of this patent is extended or adjusted under 35 U.S.C. 154(b) by 366 days.

(21) Appl. No.: 12/912,810

(22) Filed: Oct. 27, 2010

(65) Prior Publication Data

US 2011/0098663 A1    Apr. 28, 2011

Related U.S. Application Data

(60) Provisional application No. 61/255,132, filed on Oct. 27, 2009.

(51) Int. Cl.
*A61M 5/00* (2006.01)

(52) U.S. Cl.
USPC ................................. 604/288.01; 604/288.04

(58) Field of Classification Search
USPC ............................ 604/288.01, 288, 275, 93.01
See application file for complete search history.

(56) References Cited

U.S. PATENT DOCUMENTS

| | | | |
|---|---|---|---|
| 5,833,654 A | 11/1998 | Powers et al. | |
| 6,562,023 B1* | 5/2003 | Marrs et al. | 604/533 |
| 6,579,265 B1* | 6/2003 | Kihara et al. | 604/174 |
| 6,758,841 B2* | 7/2004 | Haarala et al. | 604/513 |
| 7,131,962 B1* | 11/2006 | Estabrook et al. | 604/93.01 |
| 2002/0095138 A1* | 7/2002 | Lynch et al. | 604/890.1 |
| 2003/0004520 A1* | 1/2003 | Haarala et al. | 606/108 |
| 2004/0044306 A1* | 3/2004 | Lynch et al. | 604/93.01 |
| 2005/0015075 A1 | 1/2005 | Wright et al. | |
| 2005/0065466 A1* | 3/2005 | Vedrine | 604/93.01 |
| 2005/0171502 A1* | 8/2005 | Daly et al. | 604/502 |
| 2007/0149947 A1* | 6/2007 | Byrum | 604/508 |
| 2008/0114308 A1 | 5/2008 | DiPalma et al. | |
| 2010/0057021 A1* | 3/2010 | Ishikura et al. | 604/288.01 |

OTHER PUBLICATIONS

International Search Report; International Application No. PCT/US2010/054195; International Filing Date: Oct. 27, 2010; 2 pages.
International Preliminary Report on Patentability and Written Opinion; International Application No. PCT/US2010/054195; International Filing Date: Oct. 27, 2010; 9 pages.

* cited by examiner

*Primary Examiner* — Emily Schmidt
*Assistant Examiner* — Michael J Anderson
(74) *Attorney, Agent, or Firm* — Blank Rome LLP

(57) ABSTRACT

An implantable port includes a body with a reservoir in the body, a tunnel extending from the reservoir to an outer surface of the body, a pivoting coupling connected to the body near the tunnel on the outer surface, and a stem connected to the pivoting coupling.

22 Claims, 7 Drawing Sheets

IMPLANTABLE PORT WITH A PIVOTABLY COUPLED STEM

RELATED APPLICATION

The present invention claim priority to U.S. Provisional Patent Application No. 61/255,132, filed on Oct. 27, 2009. The disclosure of which is incorporated herein by reference in its entirety in this application.

FIELD OF THE INVENTION

The present invention relates to an implantable port. In particular, the present invention relates to an implantable port that includes a pivotably coupled stem.

BACKGROUND OF THE INVENTION

Vascular access devices such as subcutaneous implantable ports are often implanted in a patient to provide access to a major vein for a period of months or years so that blood can be repeatedly drawn or so that medication and nutrients can be injected into the patient's bloodstream on a regular basis. Subcutaneous implantable ports, which are also sometimes referred to as subcutaneous access ports, may be used for giving chemotherapy, providing blood transfusions, taking blood samples, delivering intravenous (IV) fluids, providing IV medicines, and the like. Known ports have an attached catheter which is typically a soft tube that is implanted into a patient's blood vessel.

After providing a local anesthetic or some other numbing medicine, at least two incisions are made. The distal end of the catheter of the known subcutaneous implantable port is inserted through a peel-apart vascular sheath and guided to desirable location of the vasculature. The proximal end of the catheter is tunneled under the skin between the two incisions. The subcutaneous implantable port is attached to the proximal end of the catheter by a locking collar and placed in a space created under the skin often referred to as a subcutaneous port pocket. The implantable port with the catheter properly connected can be sutured in the subcutaneous port pocket.

However, during removal of the peel-apart sheath or during final positioning of the port within the subcutaneous pocket with the catheter attached, the catheter can become kinked. The peel-apart sheath usage exposes the patient to the risks of bleeding and air embolism.

Thus, there is a need in the art for an implantable port that avoids, at least, the risks associated with kinking of the catheter and using the peel-apart sheath.

SUMMARY OF THE INVENTION

Accordingly, one aspect of the invention may provide an implantable port. The implantable port includes a body with a reservoir in the body, a tunnel extending from the reservoir to an outer surface of the body, a pivoting coupling connected to the body near the tunnel on the outer surface, and a stem connected to the pivoting coupling.

In one embodiment of the present invention, the stem further comprises a tubular member. In another embodiment of the present invention, the stem further comprises a tapered end disposed at one end of the tubular member. In a further embodiment of the present invention, the stem further comprises a collar disposed in a middle portion of the tubular member.

In another embodiment of the present invention, the stem further comprises a catheter coupling mated to one end of the tubular member. In a further embodiment of the present invention, the stem further comprises a hood spaced apart from the tubular member and extending substantially over one end of the tubular member.

In another embodiment of the present invention, the tunnel further comprises a fluid seal. In a further embodiment of the present invention, the tunnel further comprises a fluid seal retainer.

Another aspect of the invention may provide an implantable port, which includes a body with a reservoir in the body, a tunnel extending from the reservoir to an outer surface of the body, a pivoting coupling connected to the body near the tunnel on the outer surface, and a stem connected to the pivoting coupling. The pivoting coupling includes at least one arm that extends from the body near the tunnel and an aperture in the arm. The stem includes a protrusion on the stem that is received in the aperture.

Yet another aspect of the invention may provide an implantable port, which includes a body with a reservoir in the body, a tunnel extending from the reservoir to an outer surface of the body, a pivoting coupling connected to the body near the tunnel on the outer surface, and a stem connected to the pivoting coupling. The stem includes a tubular member, a tapered end at one end of the tubular member, a collar in a middle portion of the tubular member, a catheter coupling mated to another end of the tubular member, and a hood spaced apart from the tubular member and extending substantially over tapered end.

In one embodiment of the present invention, the pivoting coupling further comprises at least one arm that extends from the body near the tunnel, an aperture disposed in the at least one arm, and a protrusion disposed on the stem that is received in the aperture.

One aspect of the invention may provide an implantable port comprising a body with at least one reservoir within the body, a tunnel extending from the at least one reservoir to an outer surface of the body, a pivoting coupling coupled to the body near the tunnel on the outer surface, and a stem coupled to the pivoting coupling, wherein the pivot coupling allows the stem to move laterally toward or away from the body between a first position and a second position, and pivotally in relation to the body.

In one embodiment of the present invention, the stem further comprising a tubular member, wherein the tubular member is configured to engage the tunnel.

In another embodiment of the present invention, the tunnel further comprises a fluid seal, forming a fluid tight connection between the tunnel and tubular member when the stem is in the second position.

In a further embodiment of the present invention, the fluid seal comprising an O-ring deposited at one end of the tunnel close to the outer surface, wherein the tubular member is configured to enter through the O-ring and partially into the tunnel when the stem is moving into the second position from the first position.

In another embodiment of the present invention, the implantable port further comprises a securement mechanism for securing the stem in the second position.

In another embodiment of the present invention, the pivoting coupling further comprising at least one arm that extends from the body near the tunnel, wherein the at least one arm supports the stem and allowing the stem to move laterally and pivot in relative to the body.

In another embodiment of the present invention, the pivoting coupling further comprises a grove extending partially though a length of the at least one arm, and at least one protrusion on an exterior surface of the stem.

In another embodiment of the present invention, the pivoting coupling further comprises a grove extending partially though a length of the stem, and at least one protrusion on an exterior surface of the at least one arm.

In another embodiment of the present invention, the body comprises one reservoir.

In another embodiment of the present invention, the body comprises two reservoirs.

In another embodiment of the present invention, the port comprises two tunnels.

In another embodiment of the present invention, the stem further comprising two tubular members, wherein each of the tubular members is configured to engage one tunnel.

In another embodiment of the present invention, each of the tunnels further comprises a fluid seal, forming a fluid tight connection between one tunnel and one tubular member when the stem is moving into the second position from the first position.

In another embodiment of the present invention, the fluid seal comprising an O-ring deposited at one end of the tunnel close to the outer surface, wherein one tubular member is configured to enter through the O-ring and partially into one tunnel when the stem is moving into the second position from the first position.

In another embodiment of the present invention, the port comprising one stem.

In another embodiment of the present invention, the stem comprising two prongs, wherein each of the prongs is in fluid communication with a tubular member and a tunnel.

In another embodiment of the present invention, the two prongs are configured to receive a dual lumen catheter.

In another embodiment of the present invention, the port comprising two stems that may be pivoted or laterally moved independent of each other.

In another embodiment of the present invention, each of the stems is in fluid communication with a tunnel through a tubular member.

In another embodiment of the present invention, each of the stems is configured to receive a catheter.

In another embodiment of the present invention, the stem comprises a tubular member, a tapered end disposed at one end of the tubular member; a collar disposed in a middle portion of the tubular member and a hood spaced apart from the tubular member and extending substantially over tapered end.

Other objects, advantages and salient features of the invention will become apparent from the following detailed description, which, taken in conjunction with the annexed drawings, discloses a preferred embodiment of the present invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

The advantages of the present invention will be apparent to those skilled in the art from the following specification. Accordingly, it will be recognized by those skilled in the art that changes or modifications may be made to the below described embodiments without departing from the broad inventive concepts of the invention. It should therefore be understood that this invention is not limited to the particular embodiments described herein, but is intended to include all changes and modifications that are within the scope and spirit of the invention. The words "proximal" and "distal" refer to directions away from and closer to the insertion tip, respectively, of a catheter of the present invention.

Figure 1:
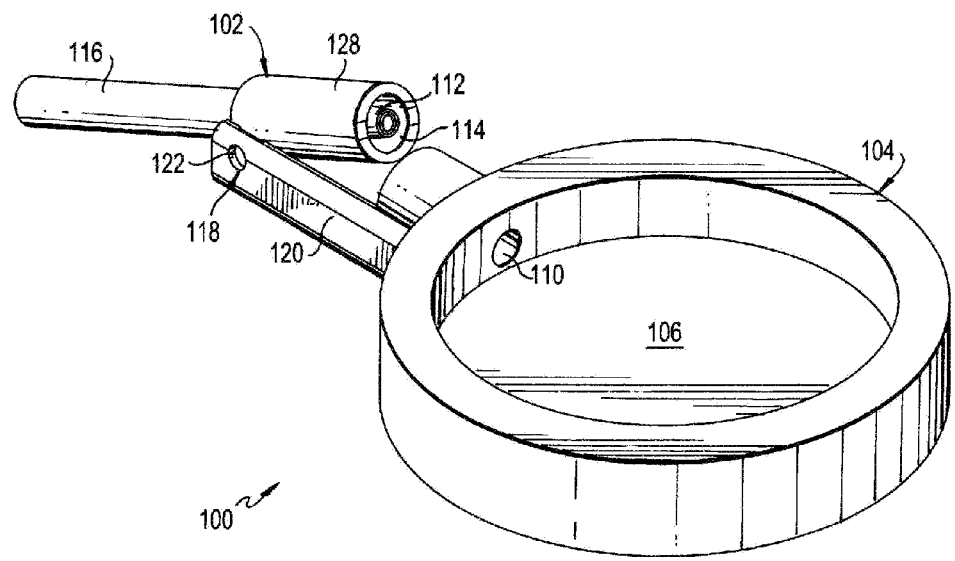
FIG. 1 is a perspective view of an implantable port with a pivotably coupled stem in a first position in accordance with an embodiment of the invention (for simplicity, only the reservoir of the implantable port body and the pivotably coupled stem is shown)
Figure 2:
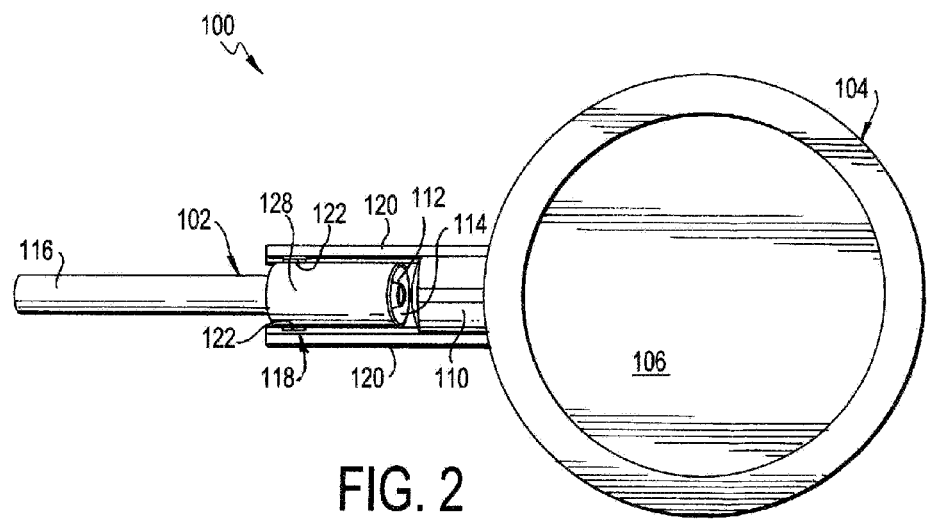
FIG. 2 is an overhead plan view of the implantable port shown in FIG. 1.
Figure 3:
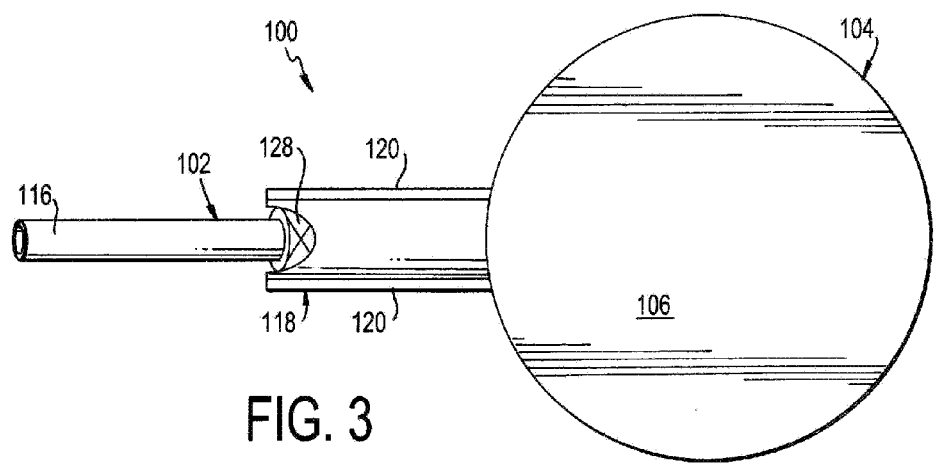
FIG. 3 is an underside plan view of the implantable port shown in FIG. 1.
Figure 4:
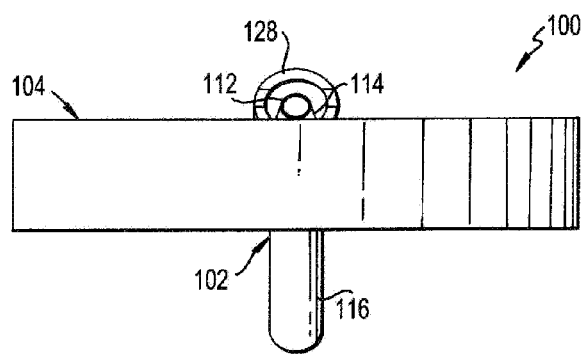
FIG. 4 is a front elevational view of the implantable port shown in FIG. 1.
Figure 5:
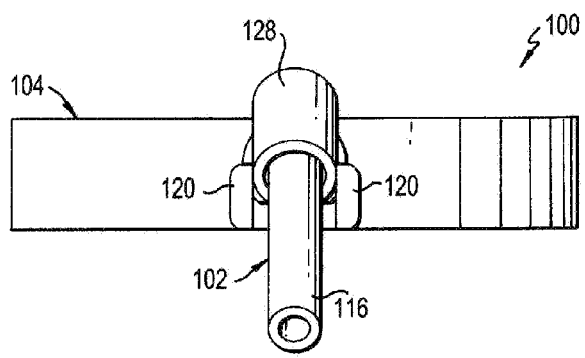
FIG. 5 is a rear elevational view of the implantable port shown in FIG. 1.
Figure 6:
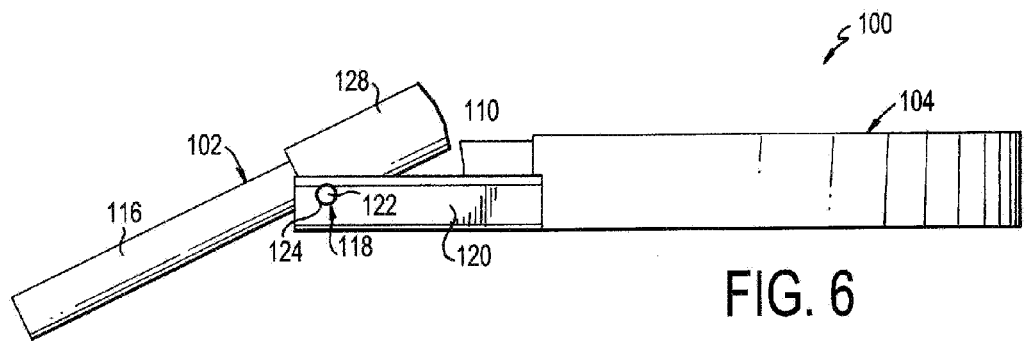
FIG. 6 is a side elevational view of the implantable port shown in FIG. 1.
Figure 7:
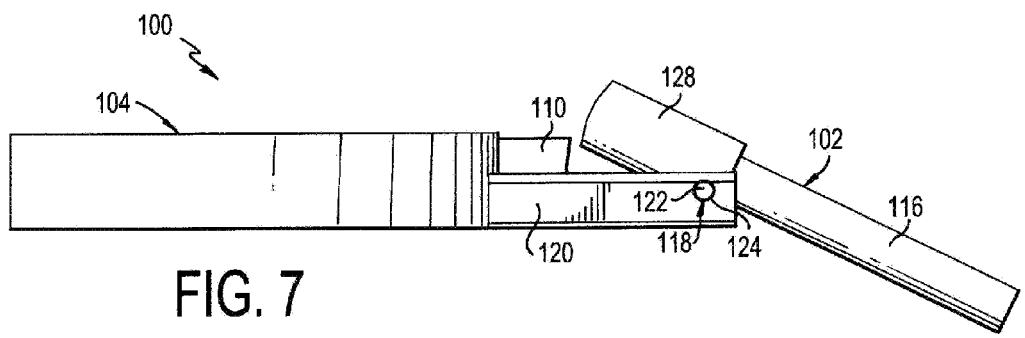
FIG. 7 is an opposite side elevational view of the implantable port shown in FIG. 1.
Figure 8:
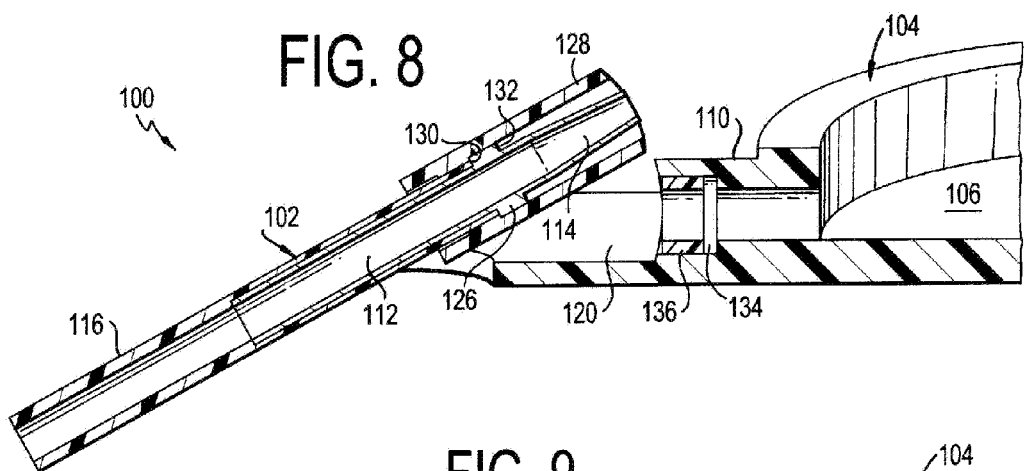
FIG. 8 is a partial sectional view of the implantable port shown in FIG. 1.
Figure 9:
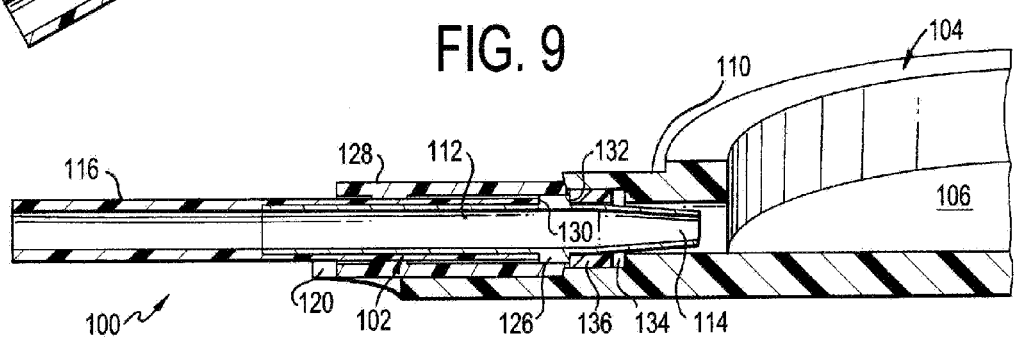
FIG. 9 is a partial sectional view of the implantable port in a second position.
Figure 10:
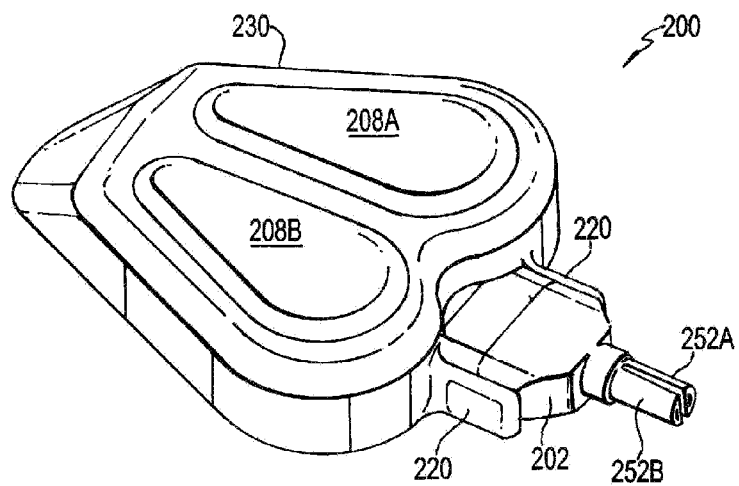
FIG. 10 is a perspective view of an implantable port with a pivotably coupled stem in a second position in accordance with a second embodiment of the invention, showing the pivotable stem in the closed position.
Figure 11:
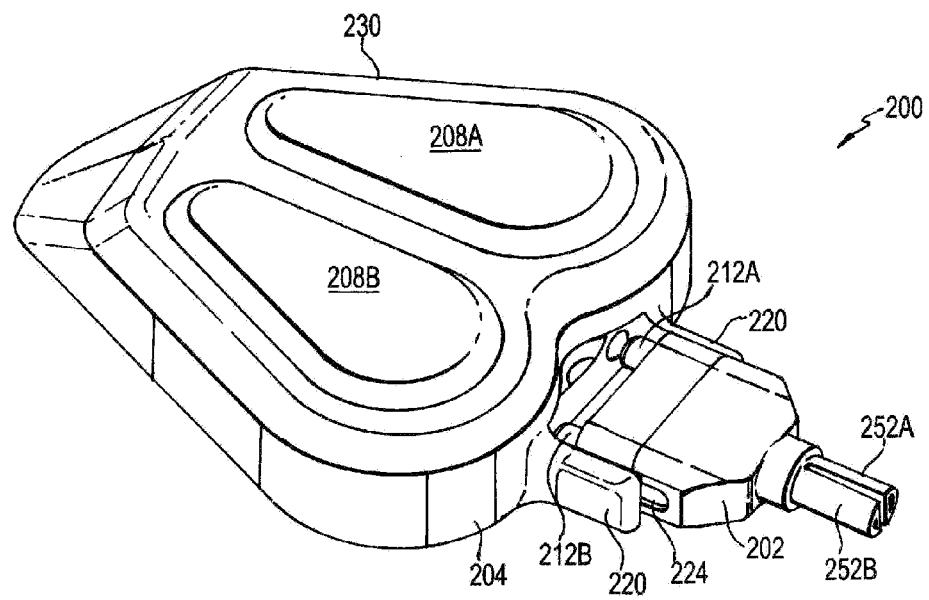
FIG. 11 is a perspective view of the implantable port of FIG. 10, showing the pivotable stem in the extended position.
Figure 12:
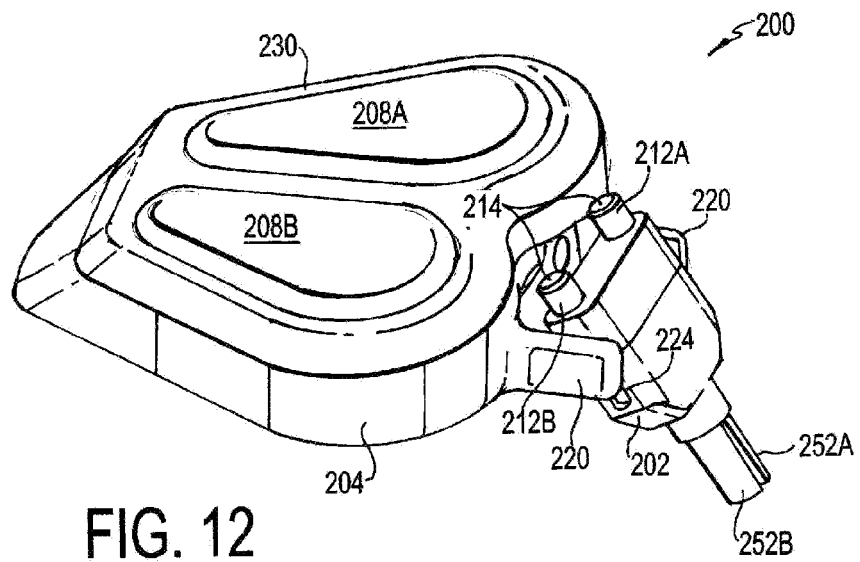
FIG. 12 is a perspective view of the implantable port of FIG. 10, showing the pivotable stem in the open position.
Figure 13:
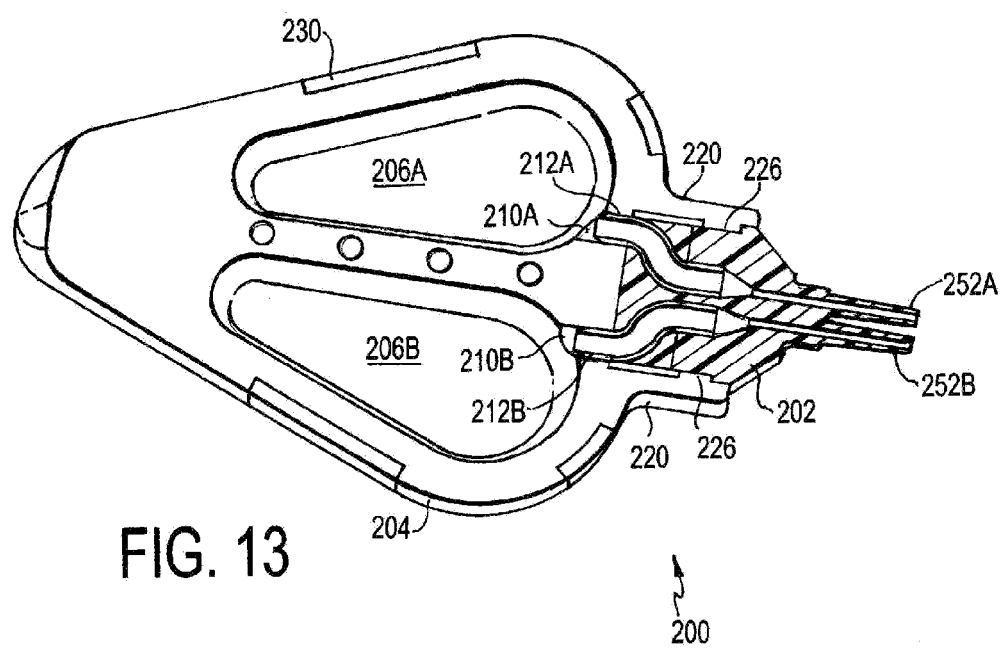
FIG. 13 is a cross section view of the implantable port of FIG. 10, showing the pivotable stem in the closed position.
Figure 14:
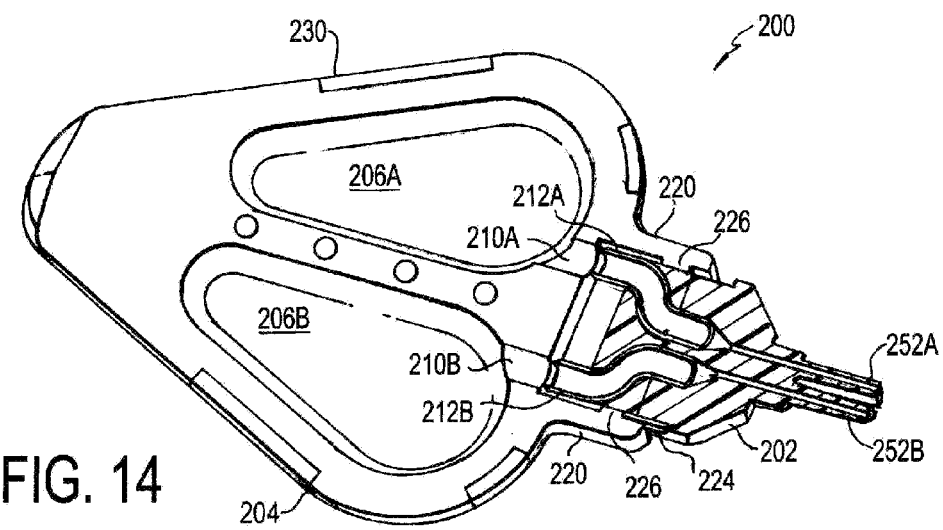
FIG. 14 is a cross section view of the implantable port of FIG. 10, showing the pivotable stem in the extended position.

Referring to FIGS. 1-9, the present invention provides an implantable port 100 that includes a pivotably coupled stem 102. The stem 102 is pivotably coupled at one end to a body 104 of the port 100, and at the opposite end, the stem 102 is adapted to be mated to a catheter (not shown). The stem 102 can be selectively placed in a first position wherein the stem 102 is not coupled to the body 104 of the port 100, as shown in FIGS. 1-8 or in a second position wherein the stem 102 is coupled to the body 104 of the port 100, as shown in FIG. 9. In the first position, a guide wire can be inserted into the stem 102 to unkink a catheter mated to the stem 102. Also, the port 100 can avoid the use of a sheath by placing over a guide wire. Thus, the port 100 avoids, at least, the risks associated with kinking of the catheter and the vascular sheath.

The body 104 can have one or more hollows within the body 104. At least one of the hollows provides a reservoir 106 to receive fluid, such as IV fluids, IV medicines, blood, or some other such fluid. The implantable port 100 can also have a septum 108 (not shown) that extends from an outer surface of the body 104 to the reservoir 106. The septum 108 allows an appropriate needle, such as a Huber needle, to access the reservoir 106, thus the septum 108 can be self-sealing after the needle is removed and can be punctured repeatedly before substantially weakening. The body 104 may have a tunnel 110 that provides a pathway between the reservoir 106 and an outer surface of the body 104. The tunnel 110 may be flush with a surface of the body 104 or may protrude away from the body 104, as shown in the figures.

In the exemplary embodiment shown in FIGS. 1-9, the body 104 has a generally cylindrical-like shape with a single reservoir 106. However, the body 104 can have any suitable shape including, but not limited to, substantially spherical, conical, ovoidal, combinations of the aforementioned, or some other shape that provides at least one hollow within the body 104. Also, the single body 104 or the single reservoir 106 shown is not meant to be limiting to the invention. In other embodiments, more than one reservoir 106 can be disposed in the body 104. In other embodiments, the implantable port 100 can have more than one body 104, and more than one reservoir can be disposed in each of the bodies. The exact number of bodies 104 and reservoirs 106 is determined by, for example, the purpose of the implantable port 100. In the depicted embodiment, the tunnel 110 has a substantially circular cross-section, but in other embodiments, the tunnel 110 can have any other suitable cross-sectional shape, such as elliptical, triangular, square, trapezoidal, polygonal, combinations of the aforementioned, or some other suitable shape.

The body 104 can be made from plastic such as biocompatible, medical grade polymers such as polysulfone, metal such as titanium, alloys such as stainless steel, rubber, synthetic rubber, glass, ceramic, combinations of the aforementioned, or some other suitable material. The body 104 can be made from a single material, a single material with one or more coatings of another material, or a single material with at least one plating of another material. The body 104 can be substantially rigid such that the reservoir 106 generally retains its shape and can resist penetration by a needle, such as the type generally used to access an implantable port (e.g., Huber needle). The septum 108 is made from a self-sealing material, such as silicone rubber, that can be punctured many times before weakening significantly.

The stem 102 mates with the catheter and is pivotably coupled to the body 104 such that the stem 102 selectively provides a pathway for fluid or some other matter between the catheter and the body 104. The stem 102 includes, at least, a tubular member 112. The tubular member 112 provides a pathway for fluid or some other matter between the catheter and the tunnel 110 that leads to the reservoir 106. Thus, the tubular member 112 may have a tapered end 114 at an end that engages the tunnel 110 to minimize stubbing between an end of the tubular member 112 and the surface around the tunnel 110. The stem 102 can also include a catheter coupling 116 that couples to one end of the tubular member 112. The catheter coupling 116 is adapted to couple the catheter to one end of the tubular member 112. The catheter coupling 116 can have a surface that is ridged or knurled so that the catheter coupling 116 can better mate to the catheter or the tubular member 112.

The stem 102 is pivotably coupled to the body 104 by a pivoting coupling 118. The pivoting coupling 118 allows the stem 102 to pivot relative to the body 104. The pivoting coupling 118 can be, but not limited to, a ball and socket joint, a condyloid joint, a saddle joint, a hinge joint, a pivot joint, and the like. In the embodiment shown in FIGS. 1-9, the body 104 includes at least two arms 120 that extend from an outer surface of the body 104 near the tunnel 110. Each arm 120 has an aperture 122 that mates with a protrusion 124 that extends from the stem 102. Thus, the stem 102 can pivot with respect to the arms 120 through its protrusions 124 rotating within the aperture 122 of each arm 120, and because the arms 120 are substantially stationary with respect to the body 104, the stem 102 can pivot with respect to the body 104.

In the embodiment shown in FIGS. 1-9, the stem 102 includes the tubular member 112 with the tapered end 114 at one end and the catheter coupling 116 at the opposite end. The stem 102 further includes a collar 126 that substantially wraps around a generally middle portion of the tubular member 112 and a hood 128 that substantially extends around the collar 126 and the tapered end 114. The collar 126 is rigidly fixed to the tubular member 112 and has at least a first surface 130 and a second surface 132. The first surface 130 abuts against the catheter coupling 116; thus the catheter coupling 116 cannot slide past the collar 126 and slip over the tapered end 114 of the tubular member 112. The second surface 132 abuts against the surface around the tunnel 110; thus the tubular member 112 cannot be inserted further into the tunnel 110.

The hood 128 is disposed spaced apart from the tapered end 114 of the tubular member 112 and extends substantially over the tapered end 114. The hood 128 may also couple the catheter coupling 116 and the tubular member 112. The hood 128 includes two protrusions 124 disposed generally opposite to each other and positioned to mate with the apertures 122 of the arms 120. Although the embodiment depicted has two sets of protrusions 124 and apertures 122, in other embodiments, the port 100 may have more or less than the two sets shown.

Referring to FIGS. 8 and 9, with the depicted construction, the stem 102 including the tubular member 112, the catheter coupling 116, and the hood 128 pivot together. When the stem 102 is pivoted such that the tubular member 112 and the hood 128 are generally aligned with the tunnel 110, the tubular member 112 can be pushed or inserted into the tunnel 110. Because of the tapered end 114 of the tubular member 112, the tubular member 112 generally avoids stubbing with the surface around the opening to the tunnel 110. Once the tubular member 112 is inserted into the tunnel 110, the tubular member 112 is retained in the tunnel 110 by the O-ring.

Furthermore, the tunnel 110 may include a fluid seal 134 and a fluid seal retainer 136. The fluid seal 134 provides a substantially fluid-tight seal between the tubular member 112 and the tunnel 110. The fluid seal 134 can be, for example, an O-ring, an adhesive, tape, or some other substantially fluid-proof seal. The fluid seal retainer 136 generally maintains the fluid seal 134 within the tunnel 110. The fluid seal retainer 136 can be, but is not limited to, a washer, an O-ring, an adhesive, tape, and the like. In the embodiment shown, the fluid seal 134 is a single O-ring, but the fluid seal 134 can be multiple O-rings or a combination of different fluid seals 134. Once the tubular member 112 is inserted into the tunnel 110, the tubular member 112 is retained in the tunnel 110 by the O-ring. In other embodiments, the tubular member 112 can be retained in the tunnel 110 by pressure fitting, friction fitting, mating threads, ridges, knurls, or some other suitable mating. Also, in the embodiment shown in FIGS. 1-9, the fluid seal retainer 136 is a single washer, but in other embodiments, the fluid seal retainer 136 can be more than one washer or a combination of a washer, an O-ring, an adhesive, tape, and the like. The implantable port of the present invention can be made to be compatible with power injection.

A method of using the implantable port 100 begins with gaining access to a blood vessel. For example, for venous access, a micropuncture technique can be utilized. Through the access to the blood vessel, a first guide wire is inserted, and a dilator or a sheath is placed over the first guide wire. In one embodiment, the dilator is disposed within the sheath. The sheath can have an inner lumen of approximately 0.035 inches to approximately 0.038 inches. The sheath may be sized for a second guide wire. The micropuncture guide wire and dilator are removed and a large 0.035"-0.038" guide wire is inserted centrally.

Local anesthesia can be applied to an area wherein the port 100 is to be inserted or the port pocket. For example, the area can be generally in the upper chest. The port pocket can be disposed at the skin entry site for tunneling by, for example, a variant longitudinal incision. Then, a hollow tunneler is advanced through the tissue in the area wherein the port 100 is to be inserted. Afterwards, the 0.035"-0.038" guide wire is directed toward the hollow tunneler. Once the guide wire reaches the hollow tunneler, the second guide wire is inserted through the hollow tunneler and directed toward the area of the port pocket.

The port 100 is placed in the port pocket with the stem 102 in the first position. That is, the stem 102 is not coupled to the body 104 of the port 100. A catheter is then placed over the guide wire. Once the catheter reaches the appropriate position, the guide wire can be removed. The catheter can then be cut to an appropriate length. Next, the catheter is coupled to the stem 102, and the stem 102 is pivoted and coupled to the body 104 of the port 100. Then, the port 100 may be flushed and the site of the incision for the port pocket can be closed.

Although one method of using the port 100 is described, the port 100 can be used with a variety of other methods and not limited to the method described. For example, the described method does not require a peel-apart vascular sheath, but such a sheath may be used with the port 100.

Referring to FIGS. 10-14, the present invention provides a second embodiment of an implantable port 200 that includes a pivotably coupled stem 202. The stem 102 is pivotably coupled at one end to a body 204 of the port 200, and at the opposite end, the stem 202 is adapted to be mated to a catheter (not shown). In this particular embodiment, the implantable port 200 is of a heart shape, and comprises two reservoirs. Each of the two reservoirs 206A 206B are within the body 204 of the implantable port 200. Each of the reservoir 206A 206B is capped with a needle penetrable septum 208A 208B respectively. The septa 208A 208B are secured by a cap 230 that attaches to the body 204 of the implantable port 200. Each of the reservoir 206A 206B comprises a tunnel 210A 210B allowing fluid communication with the reservoirs 206A 206B. The distal end of the stem 202 comprises two prongs 252A 252B. In this embodiment, the two prongs are of a generally "D" shaped cross section. A dual lumen catheter (not shown) may be secured to the prongs 252A 252B using a coupling or locking device (not shown) well known to one skilled in the art. The stem 202 of embodiment shown also has two proximal tubular members 212A 212B. The tubular members 212A 212B corresponds to the tunnels 210A 210B of the body of the implantable port 200. The stem 202 can be selectively placed in a closed position (FIG. 10), wherein the stem 202 is coupled to the body 204 of the port 200, an extended position (FIG. 11) wherein the stem 202 slides distally away from the body 204, or an open position (FIG. 12), wherein the stem 202 pivots away from the body 204 of the port 200 allowing access to the proximal tubular members 212A 212B. In the open position, a guide wire can be inserted into the each tubular members 212A 212B of the stem 202 to unkink a catheter mated to the stem 202.

The stem 202 mates with the catheter and is pivotably coupled to the body 204 such that the stem 102 selectively provides a pathway for fluid or some other matter between the catheter and the body 204. In the embodiment shown in FIGS. 10-14, the first reservoir 206A is in fluid communication with tunnel 210A, tubular member 212A and the first distal prong 252A. The second reservoir 206B is in fluid communication with tunnel 210B, tubular member 212B and the second distal prong 252B. The tubular members 212A 212B may each have a tapered end 214A and 214B at an end that engages the tunnels 210A 210B, respectively. It is contemplated in the embodiment shown in FIGS. 10-14, the tubular members 212A 212B extend into the tunnels 210A 210B when the implantable port 200 transitions from the extended position to the closed position. The stem 202 slides toward the body 204 of the implantable port. A fluid seal is achieved by using an O-ring affixed at the distal end of the tunnels 210A 210B. The O-ring typically has an inner diameter that is slightly smaller than the outer diameter of the tubular members 212A 212B. When sliding toward the body 204 of the implantable port 200, the tapered ends 214A 214B facilitates the tubular members 212A 212B to slide into the O-ring achieving a fluid seal. Alternatively, the O-ring may be of a size comparable to the diameter of the tapered ends 214A 214B, and the tapered ends 214A 214B may be pressed against the O-ring to achieve a fluid seal. Other technique for achieving a fluid seal between the tunnels 210A 210B and the tubular members 212A 212B may be employed without departing from the teaching of the present invention. A tongue and grove, a detent, or any other mechanical engagement mechanism may be used to retain the stem 202 in the closed position in relation to the body 204 of the implantable port.

The stem 202 is pivotably coupled to the body 204 by a pivoting coupling. The pivoting coupling allows the stem 202 to pivot relative to the body 204. The pivoting coupling can be, but not limited to, a ball and socket joint, a condyloid joint, a saddle joint, a hinge joint, a pivot joint, and the like. In the embodiment shown in FIGS. 10-14, the body 204 includes at least two arms 220 that extend from an outer surface of the body 204. In the particular embodiment, the arms 220 are joined at the bottom forming a U-shaped support. Each arm 220 has a protrusion 226 close to the distal end of the arm 220. The stem 202 comprising a grove 224 in a portion of the surface opposing the protrusions 226 of the arms 220 along the length of the stem 202, but does not extend all the way to the distal end. When assembled, the protrusions 226 fit in the groves 224 of the arms 220 allowing the stem 202 to slide along the arm 220, and pivot when the proximal end of the stem 202 clears the body 204 of the implantable port 200. To close the implantable port 200, the stem 202 is aligned with the arms 220, and slid toward the body 204 until the securely engages the body. To open the implantable port 200, the stem 202 is pulled away from the body 204, and then pivots to allow access to the distal tubular members 212A 212B.

The body 204 and the stem 202 can be made from plastic such as biocompatible medical grade polymers such as polysulfone, metal such as titanium, alloys such as stainless steel, rubber, synthetic rubber, glass, ceramic, combinations of the aforementioned, or some other suitable material. The body 204 and the stem 202 can be made from a single material, a single material with one or more coatings of another material, or a single material with at least one plating of another material. The body 204 can be substantially rigid such that the reservoirs 206A 206B generally retains its shape and can resist penetration by a needle, such as the type generally used to access an implantable port (e.g., Huber needle). The septa 208A 208B is made from a self-sealing material, such as silicone rubber, that can be punctured many times before weakening significantly. The tubular members 212A 212B and the distal prongs 252A 252B may be made of similar biocompatible materials as the body 204, particularly may be made of metal such as titanium and alloys such as stainless steel.

Figure 15:
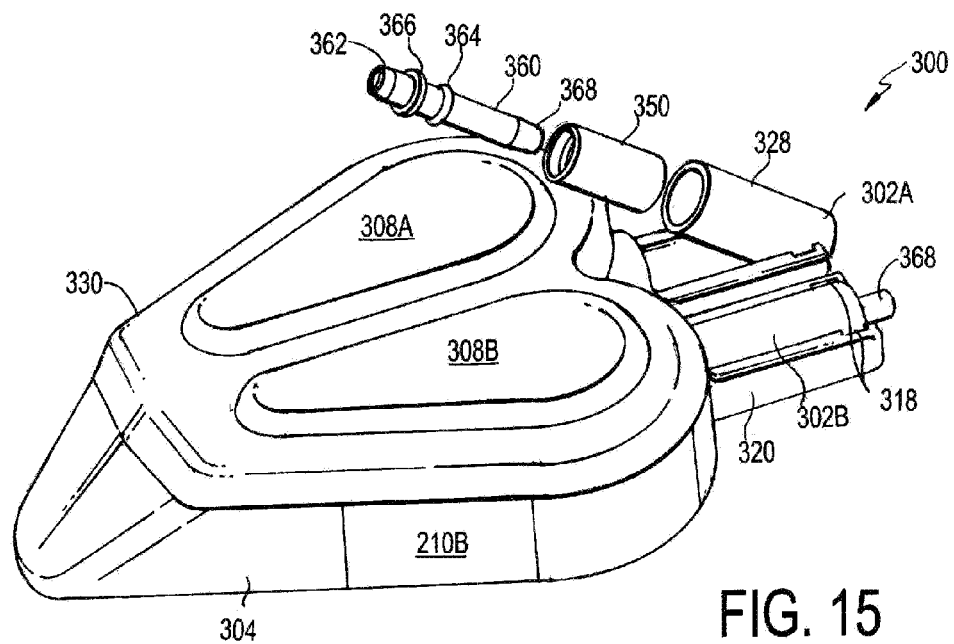
FIG. 15 is a perspective view of an implantable port with a pivotably coupled stem in a first position in accordance with a third embodiment of the invention, showing a first pivotable stem in the extended position, and an exploded view of a second pivotable stem in the opened position.
Figure 16:
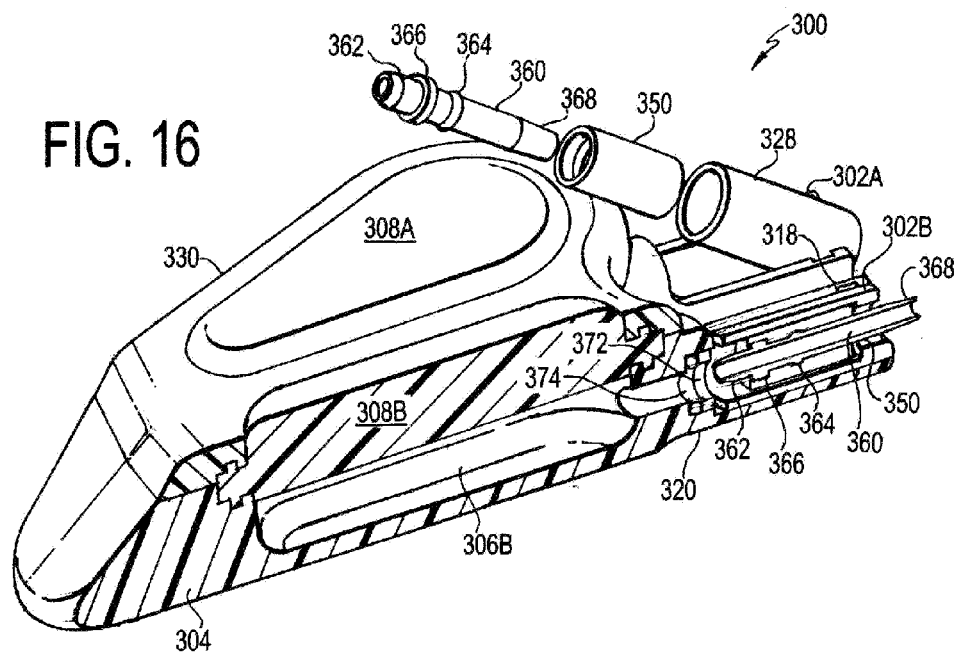
FIG. 16 is a cross section view of the implantable port of FIG. 15 in a plane along the longitudinal axis of the first pivotable stem perpendicular to the base of the implantable port.
Figure 17:
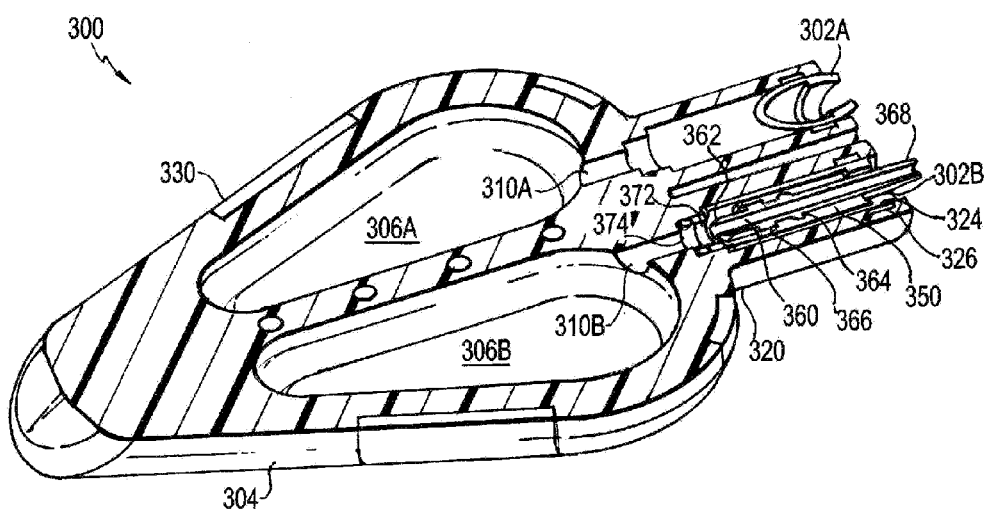
FIG. 17 is a cross section view of the implantable port of FIG. 15 in a plane parallel to the base of the implantable port.

Referring to FIGS. 15-17, the present invention provides a third embodiment of an implantable port 300 that includes two identical individual pivotable stems 302A 302B. The stems 302A 302B are pivotably coupled at one end to a body 304 of the port 300, and at the opposite end, each of the stem 302 is adapted to be mated to an individual catheter (not shown). In this particular embodiment, the implantable port 300 is of a heart shape, and comprises two reservoirs 306A 306B. Each of the two reservoirs 306A 306B are within the body 304 of the implantable port 300. Each of the reservoir 306A 306B is capped with a needle penetrable septum 308A 308B, respectively. The septa 308A 308B are secured by a cap 330 that attaches to the body 304 of the implantable port 300. Each of the reservoir 306A 306B comprises a tunnel 310A 310B allowing fluid communication with the reservoirs 306A 306B.

In the embodiment shown in FIGS. 15-17, stem 302A is shown in an exploded view. Each stem 302A 302B comprises a hood 328, a sleeve 350, and a tubular member 360. The tubular member 360 further comprises a proximal tapered end 362, a collar 364, a ridge 366, and a distal tapered end 368. The catheter is secured between the tubular member 360 and the sleeve 350. The collar 364 of the tubular member and the corresponding internal profile of the sleeve, e.g., narrowing in the inner diameter of the sleeve, compress against the catheter, ensuring a secure and fluid tight connection. The catheter, tubular member 360, and sleeve 350 assembly is placed in the hood 328. The catheter, tubular member 360, and sleeve 350 assembly may slide within the hood. When the catheter, tubular member 360, and sleeve 350 assembly slide toward and couple to the body 304, a fluid tight connection is formed from the reservoirs 306A 306B to the catheters. When the catheter, tubular member 360, and sleeve 350 assembly slide away from the body, the entire stem 302A 302B can then pivot in relation to the body 304 of the implantable port 300. Typically, the tubular member 360 is partially inserted into the catheter up to the ridge 366. The distal tapered end 368 can facilitate the insertion of the tubular member 360 into the catheter.

The stems 302A 302B mate with the catheter and is pivotably coupled to the body 304 such that the stem 302A 302B selectively provides a pathway for fluid or some other matter between the catheter and the body 304. In the embodiment shown in FIGS. 15-17, the first reservoir 306A is in fluid communication with tunnel 310A, and tubular member 360. The second reservoir 306B is in fluid communication with tunnel 310B, and tubular member 360.

Each of the stem 302A 302B can be selectively placed in a closed position, wherein the stem 302A 302B is coupled to the body 304 of the port 300, an extended position (FIG. 15-17, 302B) wherein the catheter, tubular member 360, and sleeve 350 assembly slides distally away from the body 304, or an open position (FIG. 15-16, 302A), wherein the stem 302A 302B pivots away from the body 304 of the port 300 allowing access to the proximal tubular members 382. In the open position, a guide wire can be inserted into the each tubular members 360 of the stem 302A 302B to unkink a catheter mated to the stem 302.

The tubular members 360 may each have a tapered end 362 at an end that engages the tunnels 310A 310B, respectively. It is contemplated in the embodiment shown in FIGS. 15-17, that the distal end of the tubular members 362 extend into the tunnels 310A 310B when the implantable port 300 transitions from the extended position to the closed position. A fluid seal is achieved by using an O-ring 374 affixed at the distal end of the tunnels 310A 310B. The O-ring typically has an inner diameter that is slightly smaller than the outer diameter of the tubular members 360. The O-ring 374 is secured in place by a retainer ring 372. When sliding toward the body 304 of the implantable port 300, the tapered ends 362A 362B facilitates the tubular members 360 to slide into the O-ring achieving a fluid seal. Alternatively, the tapered ends 362 may be pressed against the O-ring to achieve a fluid seal. Other technique for achieving a fluid seal between the tunnels 310A 310B and the tubular members 360 may be employed without departing from the teaching of the present invention. A tongue and grove, a detent, or any other mechanical engagement mechanism may be used to retain the stem 302 in the closed position in relation to the body 204 of the implantable port.

Each of the stems 302A 302B is pivotably coupled to the body 304 by a pivoting coupling 318. The pivoting coupling 318 allows the stem 302 to pivot relative to the body 304. The pivoting coupling 318 can be, but not limited to, a ball and socket joint, a condyloid joint, a saddle joint, a hinge joint, a pivot joint, and the like. In the embodiment shown in FIGS. 15-17, the body 304 includes at least two arms 320 that extend from an outer surface of the body 304 for each of the stems 302A 302B. In the particular embodiment, the arms 320 for each of the stem 302A 302B are joined at the bottom, forming a U-shaped support. Each stem 302A 302B has a pair of protrusions 326 close to the distal end of the stem 302A 302B. Each of the arm 320 comprising a depression 324 in the surface opposing the protrusions 326 of the stem 302A 302B. When assembled, the protrusions 326 of the stem 302A 302B fit in the depressions 324 of the arms 320 allowing the stems 302A 302B to pivot when the proximal end of the tubular members 362 clear the body 304 of the implantable port 300. To close the implantable port 300, the stem 302A 302B is aligned with the arms 320, and the catheter, tubular member 360, and sleeve 350 assembly slid toward the body 304 until it securely engages the body. To open the implantable port 300, the catheter, tubular member 360, and sleeve 350 assembly is pulled away from the body 304, and then the stem 302A 302B pivots to allow access to the distal tubular members 362.

The body 304 and the stem 302A 302B can be made from plastic such as biocompatible, medical grade polymers such as polysulfone, metal such as titanium, alloys such as stainless steel, rubber, synthetic rubber, glass, ceramic, combinations of the aforementioned, or some other suitable material. The body 304 and the stem 302 can be made from a single material, a single material with one or more coatings of another material, or a single material with at least one plating of another material. The body 304 can be substantially rigid such that the reservoirs 306A 30613 generally retains its shape and can resist penetration by a needle, such as the type generally used to access an implantable port (e.g., Huber needle). The septa 308A 308B is made from a self-sealing material, such as silicone rubber, that can be punctured many times before weakening significantly. The stem 302A 302B and its components, the tubular members 360, the sleeves 350, and the hood 328 may be made of similar biocompatible materials as the body 304. Particularly, the tubular member 360 may be made of metal such as titanium and alloys such as stainless steel.

While a particular embodiment has been chosen to illustrate the invention, it will be understood by those skilled in the art that various changes, modifications, and combinations can be made therein without departing from the scope of the invention as defined in the appended claims. Particularly, the embodiments of the pivot stem implantable port 200 300 are shown in the form of dual reservoir ports. However, the same coupling mechanism may be used in single reservoir ports or ports with more than two reservoirs.

What is claimed is:

1. An implantable port, the port comprising:
 a body with at least one reservoir within the body and at least one tunnel within the body, the at least one tunnel extending from the at least one reservoir to an outer surface of the body;
 a pivoting coupling communicating with the body near the at least one tunnel on the outer surface of the body; and
 at least one stem communicating with the pivoting coupling;
  wherein the pivoting coupling allows the at least one stem to move between a first position, where the at least one stem is not coupled to the body, and a second position, where the at least one stem is coupled to the body; and
  wherein, when in the first position, the pivoting coupling allows the at least one stem to move laterally toward or away from the body and to pivot relative to the body while the at least one stem is movably attached to the pivoting coupling.

2. The implantable port of claim 1, wherein the at least one stem further comprises at least one tubular member configured to securely engage the at least one tunnel of the body when the at least one stem is in the second position.

3. The implantable port of claim 1, wherein the pivoting coupling includes at least one arm that extends from the body near the at least one tunnel, wherein the at least one arm supports the at least one stem in the first and in the second positions, wherein the at least one stem, when in the first position, is configured to move laterally relative to the at least one arm and to pivot relative to the at least one arm.

4. The implantable port of claim 3, wherein the at least one arm includes at least one aperture, and the at least one stem includes at least one protrusion, wherein the at least one stem pivots relative to the at least one arm by the at least one respective protrusion rotating within the at least one respective aperture.

5. The implantable port of claim 1, wherein the body comprises two reservoirs and two tunnels, where a respective tunnel extends from a respective reservoir to an outer surface of the body, and the stem further comprises two tubular members, wherein each tubular member is configured to securely engage a respective tunnel of the body when the at least one stem is in the second position.

6. The implantable port of claim 5, wherein one stem includes the two tubular members, wherein, when the one stem is in the second position, each tubular member is configured to securely engage a respective tunnel of the body.

7. The implantable port of claim 6, wherein the one stem further comprises two prongs, where each prong is in fluid communication with a respective tubular member and tunnel, and where the two prongs are configured to receive a dual lumen catheter.

8. The implantable port of claim 5, wherein two stems are included, each stem including a respective one tubular member, wherein, when the two stems are in the second position, the two tubular members are configured to securely engage a respective tunnel of the body.

9. The implantable port of claim 1, wherein the pivoting relative to the body is pivoting about any axis other than an axis parallel to the longitudinal axis of the stem.

10. The implantable port of claim 1, wherein a longitudinal axis of the stem pivots angularly away from a longitudinal axis of the pivoting coupling.

11. The implantable port of claim 3, wherein the at least one arm supports the at least one stem by a protrusion extending from one of the at least one arm or stem, and a groove in the other of the at least one arm or stem, the pivoting coupling allowing the at least one stem to move laterally toward or away from the body, and pivot relative to the body, by interaction of the respective protrusion and groove configuration.

12. An implantable port, the port comprising:
 a body with at least one reservoir within the body and at least one tunnel within the body, the at least one tunnel extending from the at least one reservoir to an outer surface of the body;
 a pivoting coupling communicating with the body near the at least one tunnel on the outer surface of the body; and
 at least one stem communicating with the pivoting coupling;
  wherein the pivoting coupling allows the at least one stem to move between a first position, where the at least one stem is not coupled to the body, and a second position, where the at least one stem is coupled to the body;
  wherein, when in the first position, the pivoting coupling allows the at least one stem to move laterally toward or away from the body and to pivot relative to the body; and
  wherein a pivoting axis of the pivoting coupling is perpendicular to a longitudinal axis of the stem.

13. An implantable port, the port comprising:
 a body with at least one reservoir within the body and at least one tunnel within the body, the at least one tunnel extending from the at least one reservoir to an outer surface of the body;
 a pivoting coupling communicating with the body near the at least one tunnel on the outer surface of the body; and
 at least one stem communicating with the pivoting coupling;
  wherein the pivoting coupling allows the at least one stem to move between a first position where the at least one stem is not coupled to the body, and a second position, where the at least one stem is coupled to the body;
  wherein, when in the first position, the pivoting coupling allows the at least one stem to move laterally toward or away from the body and to pivot relative to the body; and
  wherein each stem includes:
   a tubular member having:
    a tapered end disposed on at least one end thereof;
    a collar disposed in a middle portion thereof;
   a sleeve having a hollow center capable of securing therein a catheter to the tubular member; and
   a hood spaced apart from the tubular member and the sleeve, wherein the sleeve may slide within the hood.

14. The implantable port of claim 13, wherein the tubular member and the sleeve may slide toward the body within the hood to engage the tubular member with a respective at least one tunnel when the stem is in the second position.

15. An implantable port, the port comprising:
a body with at least one reservoir within the body and at least one tunnel within the body, the at least one tunnel extending from the at least one reservoir to an outer surface of the body;
a pivoting coupling connected to the body near the at least one tunnel on the outer surface of the body; and
at least one stem connected to the pivoting coupling;
wherein the pivoting coupling allows the at least one stem to be selectively placed in a closed position, where the at least one stem is coupled to the body, in an extended position, where the at least one stem slides distally away from the body, and in an open position, where the stem pivots away from the body.

16. The implantable port of claim 15, wherein, when the stem pivots away from the body, a pivoting axis of the pivoting coupling is perpendicular to a longitudinal axis of the stem.

17. The implantable port of claim 15, wherein the pivoting coupling includes at least two arms that extends from the outer surface of the body, the at least two arms joined at a bottom thereof to form a U-shape support, wherein each arm has a protrusion close to a distal end of the respective arm, and the stem includes a groove in a portion of a surface thereof opposing the respective protrusions, wherein the respective protrusions fit in the respective grooves allowing the stem to slide along the two arms and to pivot when a proximal end of the stem slides away to clear the body.

18. The implantable port of claim 17, wherein, to place the stem in the closed position, the stem is pivotally aligned with the two arms and then slid toward the body until securely engaging the body.

19. An implantable port, the port comprising:
a body with at least one reservoir within the body and at least one tunnel within the body, the at least one tunnel extending from the at least one reservoir to an outer surface of the body;
a pivoting coupling connected to the body near the at least one tunnel on the outer surface of the body; and
at least one stem connected to the pivoting coupling;
wherein the pivoting coupling allows the at least one stem to pivot between a first position, where the at least one stem is not coupled to the body, and a second position, where the at least one stem is coupled to the body; and
wherein, when in the first position, the stem is pivoted about the pivoting coupling to angulate a longitudinal axis of the stem away from a longitudinal axis of the tunnel and, when in the second position, the stem is pivoted about the pivoting coupling to align the longitudinal axis of the stem with the longitudinal axis of the tunnel.

20. The implantable port of claim 19, wherein a pivoting axis of the pivoting coupling is perpendicular to a longitudinal axis of the stem.

21. The implantable port of claim 19, wherein the pivoting coupling includes at least one arm that extends from the body near the at least one tunnel, wherein the at least one arm supports the at least one stem in the first and in the second positions, wherein the at least one stem, when in the first position, is configured to move laterally relative to the at least one arm and to pivot relative to the at least one arm.

22. An implantable port, the port comprising:
a body with at least one reservoir within the body and at least one tunnel within the body, the at least one tunnel extending from the at least one reservoir to an outer surface of the body;
a pivoting coupling communicating with the body near the at least one tunnel on the outer surface of the body; and
at least one stem communicating with the pivoting coupling;
wherein the pivoting coupling allows the at least one stem to move between a first position, where the at least one stem is not coupled to the body, and a second position, where the at least one stem is coupled to the body;
wherein, when in the first position, the pivoting coupling allows the at least one stem to move laterally toward or away from the body and to pivot relative to the body;
wherein the body comprises two reservoirs and two tunnels, where a respective tunnel extends from a respective reservoir to an outer surface of the body, and the stem further comprises two tubular members, wherein each tubular member is configured to securely engage a respective tunnel of the body when the at least one stem is in the second position;
wherein two stems are included, each stem including a respective one tubular member, wherein, when the two stems are in the second position, the two tubular members are configured to securely engage a respective tunnel of the body; and
wherein the two stems may, independent of each other, when in the first position, move laterally relative to the body and pivot relative to the body.

* * * * *